Dec. 24, 1968 W. ZOMBORY ET AL Plant Pat. 2,852
DIANTHUS PLANT
Filed June 5, 1967
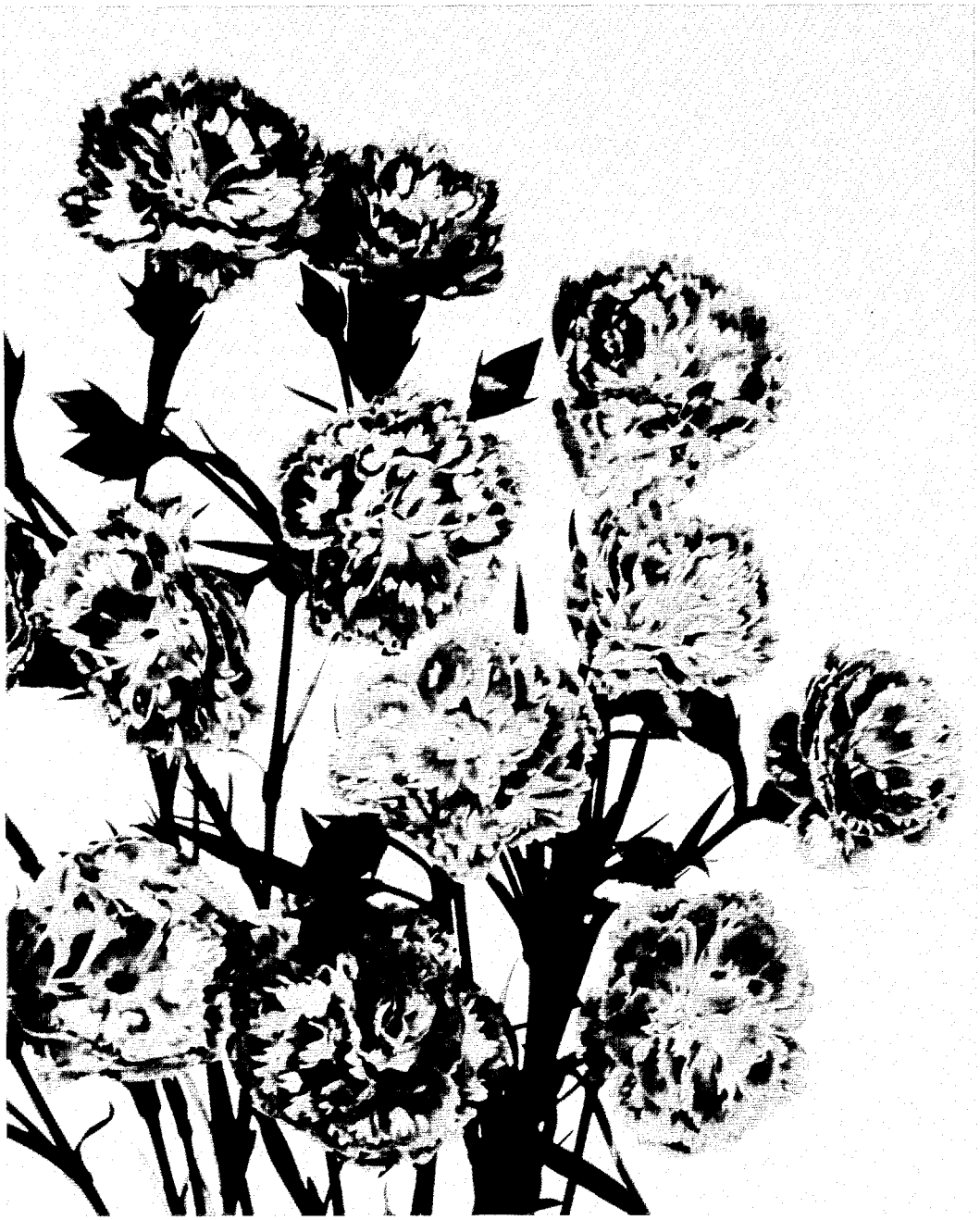
Inventors.
William Zombory
Sophia B. Zombory
By: Robb & Robb
Attorneys.

United States Patent Office

Plant Pat. 2,852
Patented Dec. 24, 1968

2,852
DIANTHUS PLANT

William Zombory and Sophia B. Zombory, Detroit, Mich., assignors to Jackson & Perkins Company, Newark, N.Y., a corporation of New York Filed June 5, 1967, Ser. No. 643,740
1 Claim. (Cl. Plt.—70)

The present invention relates to a new and distinct variety of Dianthus plant which was originated by us by crossing an unnamed and unpatented Dianthus seedling derived from an unnamed and unpatented white-flowered Dianthus seedling × an unnamed and unpatented laced, pink-flowered variety of the species botanically known as *"Dianthus allwoodi,"* with another unnamed and unpatented Dianthus seedling derived from an unnamed and unpatented show-pink *allwoodi* seedling × an unnamed and unpatented laced pink *allwoodi* seedling.

The primary objective of this breeding was to produce a new Dianthus variety having the everblooming habit and compact form of *Dianthus allwoodi,* but which bears flowers of a different color. This objective was fully achieved, along with other desirable improvements, as evidenced by the following unique combination of characteristics which are outstanding in the new variety and which distinguish it from its parents, as well as from all other varieties of which we are aware:

(1) A compact habit of plant growth;
(2) An attractive Yew Green foliage color;
(3) Pronounced fimbriated flower petals;
(4) A distinctive and attractive general color tonality of the flowers corresponding to Pomegranate Purple, with the outer edges of the petals circled with Rosolane Pink; and
(5) A spicy carnation flower fragrance.

Asexual reproduction of our new variety by cuttings, as performed at Detroit, Mich., and also at Newark, N.Y., shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with Ridgway's Color Standards and Nomenclature:

Parentage: Seedling.

*Seed parent.*—An unnamed seedling derived from an unnamed white-flowered Dianthus seedling × an unnamed laced, pink-flowered seedling.

*Pollen parent.*—An unnamed seedling derived from an unnamed show-pink *allwoodi* seedling × an unnamed laced, pink-flowered *allwoodi* seedling.

Blooming season: Starts blooming the first year from cuttings, beginning in June and continuing all through the summer to the end of September.

*Plant*

Growth: Tall (about 12 inches to 14 inches); compact.
Leaves: Many bottom leaves in tufts; about 3 inches long; narrow; medium thickness. Color—Yew Green, Plate 31.
Flower Stem: About 10 inches long; strong and stiff; from three to five flowers per stem. Color—Dark Cress Green, Plate 31.

*Flower*

Borne: Mostly on own-branched stalks; some on the laterals nearly sessile.
Size: About 2½ inches in diameter.
Petals: From 25 to 30; lacy and fimbriated. Color: upper side—Pomergranate Purple, Plate 12, with outer edge of petals circled with Rosolane Pink, Plate 26; reverse side—Pale Amaranth Pink, Plate 12, lightly overcast with Pale Rosolane Purple, Plate 26.
Claw: Color—White, Plate 53, blended with Pale Glass Green, Plate 31.
Calyx: Cylindrical and splits in open stages of the flower; teeth about ½ inch in length and erect. Color—Ivy Green, Plate 31, with teeth Courge Green, Plate 17.
Bracts: 4 in number. Color—Light Elm Green, Plate 17.
Stamens: About 5 in number. Color—White, Plate 53.
Anthers: Color—White, Plate 53.
Ovary: Oval; small.
Fragrance: Spicy carnation.

We claim:

1. A new and distinct variety of Dianthus plant, substantially as herein shown and described, characterized particularly as to novelty by the unique combination of a compact habit of plant growth, an attractive Yew Green foliage color, pronounced fimbriated flower petals, a distinctive and attractive general color tonality of the flowers corresponding to Pomegranate Purple, with the outer edges of the petals circled with Rosolane Pink, and a spicy carnation flower fragrance.

No references cited.

ROBERT E. BAGWILL, *Primary Examiner.*